United States Patent [19]

Kindt-Larsen et al.

[11] Patent Number: 5,114,240
[45] Date of Patent: May 19, 1992

[54] METHOD AND A DEVICE FOR PREPARING A MIXTURE OF A SOLID AND A LIQUID COMPONENT

[75] Inventors: Ture Kindt-Larsen, Vedbæk; Per Wolff, Birkerød; Michael Morris, Allerød, all of Denmark

[73] Assignee: Wolff & Kaaber A/S, Denmark

[21] Appl. No.: 521,733

[22] Filed: May 10, 1990

[30] Foreign Application Priority Data

May 12, 1989 [DK] Denmark .............................. 2355/89

[51] Int. Cl.$^5$ .............................................. B67B 7/24
[52] U.S. Cl. .................................. 366/129; 366/189; 222/541
[58] Field of Search ............... 366/129, 130, 332, 333, 366/348, 349, 341, 240, 289, 309; 206/219; 222/541, 136, 190; 604/224

[56] References Cited

U.S. PATENT DOCUMENTS

| | | | |
|---|---|---|---|
| 2,591,046 | 4/1952 | Brown | 222/136 |
| 3,595,439 | 7/1971 | Newby | 222/80 |
| 3,735,900 | 5/1973 | Gores | 366/129 |
| 3,831,742 | 8/1974 | Gardella et al. | 206/219 |
| 4,463,875 | 8/1984 | Tepic | 206/219 |
| 4,648,532 | 3/1987 | Green | 222/136 |
| 4,676,655 | 6/1987 | Handler | 366/332 |
| 4,799,801 | 1/1989 | Brüning | 222/136 |
| 4,973,168 | 11/1990 | Chan | 366/130 |

FOREIGN PATENT DOCUMENTS

1103969 2/1968 United Kingdom .

*Primary Examiner*—Philip R. Coe
*Assistant Examiner*—Reginald L. Alexander
*Attorney, Agent, or Firm*—Ostrolenk, Faber, Gerb & Soffen

[57] ABSTRACT

A mixing device comprises a first cylinder (10) containing a particulate or powdered component (11) and having a closed first end (13, 14) and an opposite second end which is closed by a piston-like venting and filtering assembly (12, 15). The device also comprises a second cylinder (18) containing the liquid component (19) and having a closed end (20, 22) and an opposite open end sealingly receiving the closed end of the first cylinder (10) therein in a piston-like manner. Means (14) are provided for communicating between the inner space of the first and second cylinders (10, 18) through the closed end (13, 14) of the first cylinder (10), when the first cylinder is forced into the second cylinder, whereby liquid from the first cylinder is injected into interstices defined between the particulate component contained in the first cylinder for providing a paste-like material. The communicating means is preferably formed by a breakable membrane (14). The venting and filtering assembly (12, 15) may be used as a piston for discharging the paste-like mixture made from the first cylinder (10). The mixing device is preferably used for mixing components so as to form a bone cement.

36 Claims, 6 Drawing Sheets

METHOD AND A DEVICE FOR PREPARING A MIXTURE OF A SOLID AND A LIQUID COMPONENT

BACKGROUND OF THE INVENTION

1. Field of the Invention

The present invention relates to a method of and a device for preparing a mixture of a solid, particulate or powdered component and a liquid component so as to provide a paste-like material therefrom.

2. Description of the Prior Art

Known devices of the above type are described in i.a. SE-B-7102491, CH-622752-A5, U.S. Pat. No. 4,546,767, GB-1 313 339, GB-1 413 734, DE-28 38 222-A1, WO 85/04567 and WO 86/06618.

SUMMARY OF THE INVENTION

The present invention provides an improved method of preparing a mixture of a solid, particulate or powdered component and a liquid component so as to provide a paste-like material therefrom comprises the steps of arranging the particulate or powdered component in a first cylinder, the size of the particles of said particulate component being such that coherent liquid-receiving interstices are defined therebetween, arranging the liquid component in a second cylinder having an open end and an opposite closed end, a first end of the first cylinder being arranged in the open end of the second cylinder in a piston-like manner and in sealing relation thereto, forcing said liquid into the first cylinder by forcing the first cylinder towards the closed end of the second cylinder while venting the first cylinder at a second end of the first cylinder opposite to said first end thereof, whereby the liquid is received in said interstices, and subsequently expelling said mixture of particulate material and liquid from the first cylinder.

The method according to the invention provides for an effective mixing of the two materials and subsequently a very high homogeneity of the paste-like material provided by the mixing process.

The mixture is preferably compacted prior to expelling, whereby a higher degree of homogeneity is achieved.

Subsequent to the compaction the mixture is preferably allowed to mature for a predetermined period of time prior to expelling, whereby the mixture acquires the required properties. Due to the high degree of homogeneity the necessary period of time for maturing the mixture can be very short.

According to the invention the first cylinder is preferably vented through a gas-permeable wall part or filter impermeable to the particles of the particulate or powdered component, so as to retain the particles in the cylinder during mixing and compaction, while venting it.

In the method described herein an effective dosage procedure will be provided when the mixture is expelled through said first end of the first cylinder and through an outlet opening defined in the adjacent closed end of said second cylinder surrounding said first cylinder, by means of a piston displaceably arranged in the first cylinder.

The method according to the invention may, for example, be used for mixing and expelling of acrylate bone cement compositions, such as the bone cement composition described in the applicants' U.S. Pat. No. 4,910,259 which is hereby incorporated herein by reference.

The mixing device of the invention comprises a first cylinder for containing a particulate or powdered component and having a closed first end and an opposite second end provided with venting means, a second cylinder for containing a liquid component and having a closed first end and an opposite open second end sealingly receiving the closed first end of the first cylinder therein in a piston-like manner, means for communicating between the inner spaces of the first and second cylinders through said closed first end of the first cylinder. whereby liquid from the first cylinder is injected into interstices defined between the particulate component contained in the first cylinder for providing said paste-like material when said first cylinder is forced into the second cylinder. These features provides for an instant and effective mixing of the components when the first cylinder is forced into the second cylinder so as to form the paste-like material. Furthermore, the mixing of the components is performed separated from the environment, whereby any contamination of the components and the mixture is prevented. This is essential when the mixture is to be used in connection with human tissue under surgery conditions. Possible volatile, toxic or smelling components of the mixture which may present severe problems with the known means for dosing and mixing are also effectively prevented from escaping from the mixing device of the present invention.

The communicating means may be operated in any suitable manner so as to establish communication between the inner spaces of the first and second cylinder. In the preferred embodiment such communication is automatically established by forcing the first cylinder into the second cylinder.

Preferably, the mixing device further comprises means for expelling said paste-like material from said first cylinder and these expelling means preferably comprise a piston member displaceably arranged in said second end of the first cylinder. Thus, when the mixture has been formed in the first cylinder it may be expelled by means of the piston member, for example through a spout or nozzle.

The inner spaces of the first and second cylinders may communicate through any type of valve which may, for example, be opened manually immediately before forcing the first cylinder into the second cylinder. However, according to the invention the communicating means preferably comprises a wall part of the closed first end of the first cylinder which is breakable when exposed to a predetermined first differential pressure, and in the preferred embodiment of the mixing device the breakable wall part is a breakable membrane which makes it possible to obtain a wall-defined breaking point.

In the preferred embodiment of the invention the venting means is arranged in said piston member, and it preferably comprises vapor-absorbing filtering means, such as activated carbon. These features prevent any malodorous and/or hazardous gases from escaping to the environment and a possible inconvenience and/or health risk of persons handling the device is eliminated or reduced.

The mixing device may further comprise a piston-like filter device which is displaceably arranged within the first cylinder for defining a material-receiving space between said filter device and said closed first end of the first cylinder. The particulate component may then be housed in this space.

The filter device may comprise filtering means which is penetrable to gas, but impervious to liquid, whereby any excessive amount of the liquid component in the second cylinder is prevented from flowing out from the mixing device through the filter device. As an example, the filtering device may comprise a filtering medium which swells when contacted by liquid.

The piston member of the device according to the invention preferably comprises releasable locking means for maintaining the piston member immobile in relation to the first cylinder, the locking means being released when the piston member is exposed to a second inwardly directed axial pressure substantially exceeding said predetermined first differential pressure.

This means that when the piston member is exposed to an axially inwardly directed pressure exceeding the first differential pressure, but not exceeding said second pressure, communication is established between the inner spaces of the first and second cylinders. However, the locking means of the piston member are not released. When the paste-like mixture prepared is ready to be expelled said second pressure may be applied to the piston member to release the locking means.

The locking means may comprise one or more projections extending radially from the piston member and engaging with the first cylinder or a member connected thereto.

The closed end of the second cylinder may be provided with a manually operatable valve of any kind which may be opened when the prepared mixture is to be expelled. However, in the preferred embodiment of the invention the closed first end of the second cylinder comprises a wall part which is breakable when exposed to a predetermined third differential pressure. It is further preferred that a removable back-up member is arranged in supporting engagement with the outer surface of said breakable wall part of the closed first end of the second cylinder. The back-up member ensures that the breakable wall part or membrane is supported when the mixing and compacting steps are performed. When the back-up member is removed the membrane will break upon application of a relatively low differential pressure and enable the mixture to flow out of the device and for the first time be brought into contact with the environment.

The device according to the invention may be used for storing and mixing components of any type, for example for forming an adhesive or a filler material, for example, for dental or surgical use. The device according to the invention is especially applicable for use under sterile conditions. As an example, the device according to the invention may contain a particulate component and a liquid component forming bone cement when mixed.

It is preferred that particulate component contained in the first cylinder substantially comprises particles of a size between 15 and 300μ, more preferred between 25 and 250μ, and mostly preferred between 50 and 200μ, whereby a thorough plug-flow mixing may be achieved in the device. The particles may, for example, comprise spherical particles having a size within the above ranges combined with a smaller fraction of particles of a smaller size, such as crushed particles.

In one embodiment of the invention the first cylinder contains a polymer component comprising (meth)acrylate polymers or copolymers or a mixture thereof and the second cylinder contains a liquid monomeric (meth-)acrylate.

The first cylinder may further contain X-ray contrast particles, such as barium sulfate or zirconium oxide having a size of 0.5–15μ, in an amount of up to 15 percent. When such particles are contained in the mixture it is possible on a radiograph to watch the conditions of the interface between the mixture and for instance bone tissue in the human body.

Alternatively, the X-ray contrast particles may be incorporated in the polymer particles.

Thus, according to the invention a device has been achieved which is very advantageous for storing two components for forming bone cement, for mixing the two components, for maturing the mixture and for application of the mixture under sterile conditions, and all steps take place with a minimal contact with the environment.

It should be understood that an important aspect of the invention is that the process of mixing, compressing, and expelling the mixture may be controlled by applying a series of predetermined forces to the same piston in one consecutive operation. Thus, the mixing device may contain breakable and/or releasable means which come into function when various forces are applied to the device.

A first force provides a differential pressure large enough to break the membrane separating the particulate and liquid components and to move the first cylinder to the closed end of the second or outer cylinder. A second force will release the piston member and allow the mixture to be compressed. A third force provides a third differential pressure large enough to break the membrane in the closed end of the outer cylinder and to expell the mixture. Preferable, said third differential pressure is lower than the first differential pressure. The absolute level of forces will vary with the nature of the materials and diameter of the device.

As an example, when using a device having a diameter of approximately 40 mm containing an acrylic bone cement, the force required to break the first membrane is typically 0.8–1.1 kN. To release the piston member the force is 1.3–1.7 kN and the mixture is then compressed at this or a higher force. After compression the back-up member supporting the second membrane is removed and the second membrane is broken at a force of 0.4–0.7 kN and the mixture is expelled.

BRIEF DESCRIPTION OF THE DRAWINGS

The invention will now be described in further detail with reference to the drawings, wherein.

DESCRIPTION OF THE PREFERRED EMBODIMENTS

FIGS. 1-6 illustrate a mixing device in which a particulate, solid component and a liquid component are housed completely separated in respective chambers or compartments, so that the device may be stored with the solid and liquid components in such separated condition. Immediately prior to use the solid and liquid components may be mixed so as to form a paste-like mixture, which may thereafter be expelled from the mixing device and applied to a position of use. The mixing device illustrated in the drawing is preferably intended for storing and mixing components for preparing a bone cement mixture.

Figure 1:
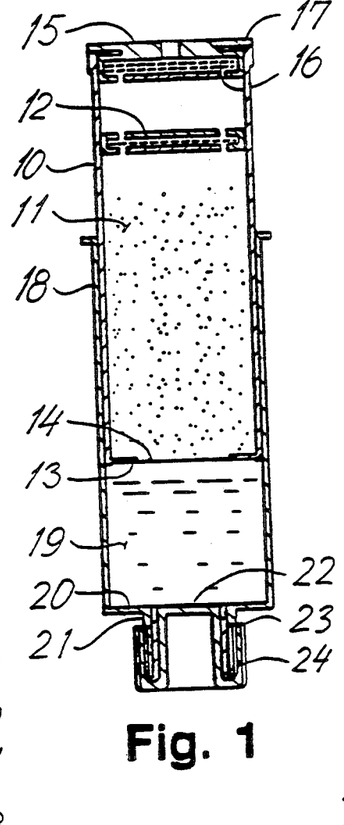
FIGS. 1–6 are diagrammatic sectional views of a mixing device according to the invention illustrating various operational steps of the mixing device.

FIG. 1 shows the mixing device in a condition ready for use and may, for example, just have been removed from a sterile packing in which it has been shipped and store. The syringe-like mixing device comprises an inner cylinder 10 defining a compartment which contains a powdered or particulate material 11, such as a polymer for a two-component bone cement mixture. Interstices defined between the particles of the particulate material and a possible unfilled space in the cylinder compartment may be filled with an inert gas, such as nitrogen. The cylinder compartment of the inner cylinder 10 is defined between a piston-like filter assembly 12, which is displaceably arranged within the inner cylinder 10, and an inner end wall 13 of the cylinder, which end wall includes a breakable membrane 14. The inner cylinder 10 has an outer open end, which is closed by a pressure application disc 15, which may comprise inner venting means 16.

The pressure plate 15 may comprise a flexible radial outer flange 17 engaging with the outer end surface of the inner cylinder 10. The pressure application disc 15 with the venting means 16, which may comprise a suitable filter medium including, for example, activated carbon, may be forced into the inner cylinder 10 in a piston-like manner when a sufficient inwardly directed force is applied to the central part of the disc 15 as will be further described below.

The inner cylinder 10 is received in an outer cylinder or housing 18. The maximum outer diameter of the inner cylinder 10 is substantially equal to or slightly exceeds the inner diameter of the outer cylinder 18 so that the outer peripheral surface of the inner cylinder 10 is in sealing engagement with the inner peripheral surface of the outer cylinder 18 in a piston-like manner. The outer cylinder or housing 18 contains a liquid component 19, such as a monomer of a two-component bone cement, in a cylinder compartment defined between the inner end wall 13 of the inner cylinder 10 and an end wall 20 of the outer cylinder 18. An axially outwardly extending spout 21 is formed on the end wall 20. A possible space of the cylinder compartment not filled with the liquid component 19 is advantageously filled with oxygen or air or another gas preventing polymerization of the monomer. The amount of the liquid component or monomer 19 contained in the outer cylinder 18 is preferably related to the amount of particulate material or copolymer 11 contained in the inner cylinder 10 so that a mixture having a correct rheology is created when the components are mixed. The amount of the liquid component or monomer 19 preferably exceeds what can be contained in the free volume defined between the particles of the copolymer 11 by about 5-10 percent based on the available free volume between the particles so as to obtain a correct rheology of the mixture. However, the amount of monomer 19 should not significantly exceed this limit because the filter of the filter assembly 12 would not be able to retain the mixed material when the amount of liquid component is too high. If a very high amount of liquid is desired or required the filter assembly 12 may comprise a Gortex ®-type material, which is pervious to air, but not to liquid. In a preferred embodiment the Gortex ®-type material is replaced by a filter material which swells when coming into contact with the liquid component 19.

The inner end of the spout 21 is closed by means of a breakable membrane 22, which may be mounted on a tubular insert member 23 received in the spout 21, and during storage before use the breakable membrane 22 may be supported by a cap-like membrane supporting member 24 screwed on the externally threaded spout 21.

The function of the mixing device shown in FIGS. 1-6 will now be further described with reference to FIGS. 2-6 illustrating various operational steps of the mixing device.

Figure 2:
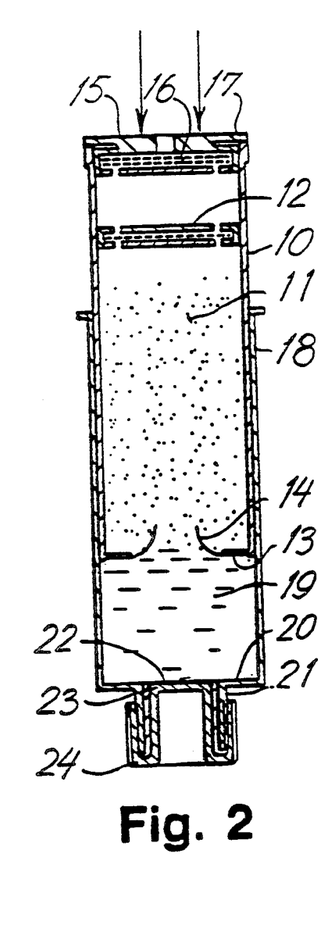

When the cartridge-like mixing device shown in FIG. 1 is to be used it may be placed in a pneumatically or mechanically operated discharge gun or discharge device (now shown) of known type by means of which an axially inwardly directed force may be applied to the central part of the pressure application disc 15 as indicated by arrows in FIG. 2. Such axially directed force tends to press the piston-like inner cylinder 10 further into the outer cylinder 18. Consequently, the component compartment containing the liquid cylinder 19 is reduced whereby the breakable membrane 14 is exposed to an increasing pressure from the liquid component. When the pressure applied to the membrane 14 exceeds a predetermined value, the membrane 14 breaks, and since an axially inwardly directed pressure on the disc 15 is maintained the inner cylinder 10 is moved inwardly into the outer cylinder 18 like a piston. The inward movement of the inner piston 10 causes the liquid component 19 contained in the outer cylinder 18 to move in a plug-flow-like manner into the interstices defined between the particles of the particulate component 11 contained in the inner cylinder 10. Gas displaced by the inflowing liquid may simultaneously escape through the filter assembly 12 and through the venting means 16 of the disc 15. The filter assembly 12 and/or the venting means 16 may comprise activated carbon or another filtering medium for absorbing hazardous or malodorous gases.

Figure 3:
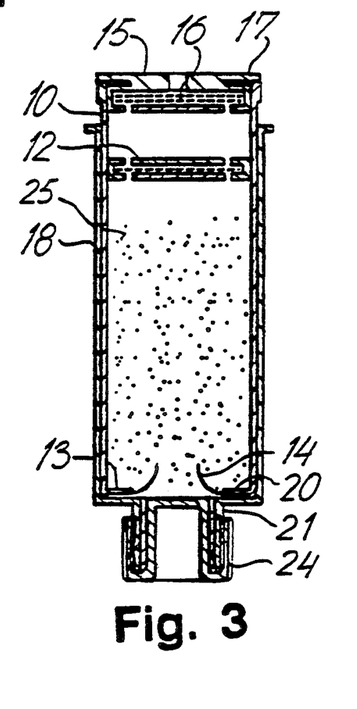
Figure 4:
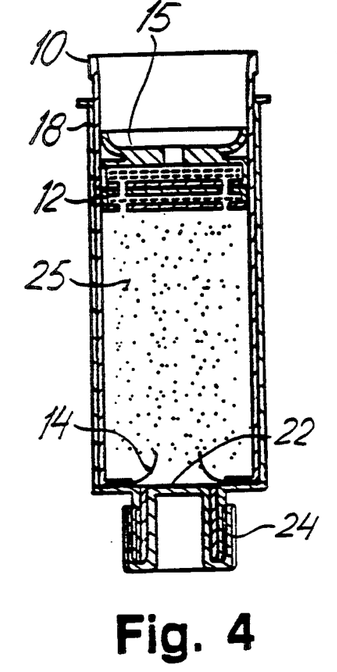

FIG. 3 show a situation where the inner cylinder 10 has been pressed completely into the outer cylinder 18 so that the inner end wall 13 of the cylinder 10 is in abutting engagement with the inner surface of the end wall 20 of the outer cylinder 18. The pressure force required to displace the inner cylinder 10 from the position shown in FIG. 2 to the position shown in FIG. 3 may, for example, be about 0.5 kN. The liquid component 19 now fills up the interstices between the particles of the particulate component 11 so that a uniform mixture 25 of the liquid and the particulate component has been obtained.

Now, the pressure force applied to the pressure application disc 15 is increased so as to flex the flange 17 of the disc sufficiently to allow the disc to be moved into the inner cylinder 10 like a piston together with the filter assembly 12. During the operations described above the mixing device is preferably positioned with the longitudinal axis of the cylinders 10 and 18 substantially vertically with the spout 21 pointing downwardly as shown in the drawings. Thus, when the filter assembly 12 reaches the upper surface of the mixture 25 this mixture of the liquid monomer and the solid polymer is gradually compacted by continuously supplying a pressure force, for example of about 3 kN, to the pressure application disc 15, whereby remaining gas in the mixture is forced out through the filter assembly 12 and the venting means 16. See FIG. 4.

Figure 5:
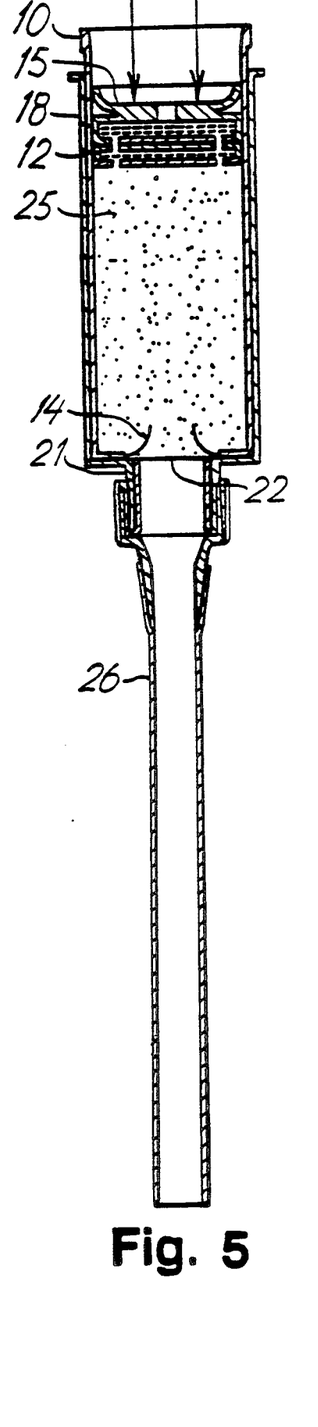

The pressure force applied to the disc 15 may now be released and the mixture 25 is allowed to mature for a period of time depending on the desired rheology of the cement product, a short maturing time period giving relatively low viscosity cement and a relatively long maturing time period giving higher viscosity or more dough-like materials. In practice, the time period chosen is influenced by factors such as the actual relationship between the amount of the liquid component and the particulate component of the mixture. The maturing time may vary from 0 to about 5 minutes and is preferably from 0.5 to 2 minutes. After the maturing period the membrane supporting member 24 is removed from the threaded spout 21 and replaced by a discharge nozzle 26 which may be screwed on the externally threaded spout 21 as shown in FIG. 5. The spout 21 is still closed by the breakable membrane 22 which is now unsupported because the supporting member 24 has been removed. When the mixture 25 has been fully matured and is ready for use an axially inwardly directed pressure force is again applied to the pressure application disc 15 as indicated by arrow in FIG. 5. The pressure transmitted to the paste-like mixture 25 causes the membrane 22 to break so that the mixture may be expelled through the spout 21 and the discharge nozzle 26 by means of which the paste-like mixture may be applied to the position of use, for example, to a bone of a patient.

Figure 6:
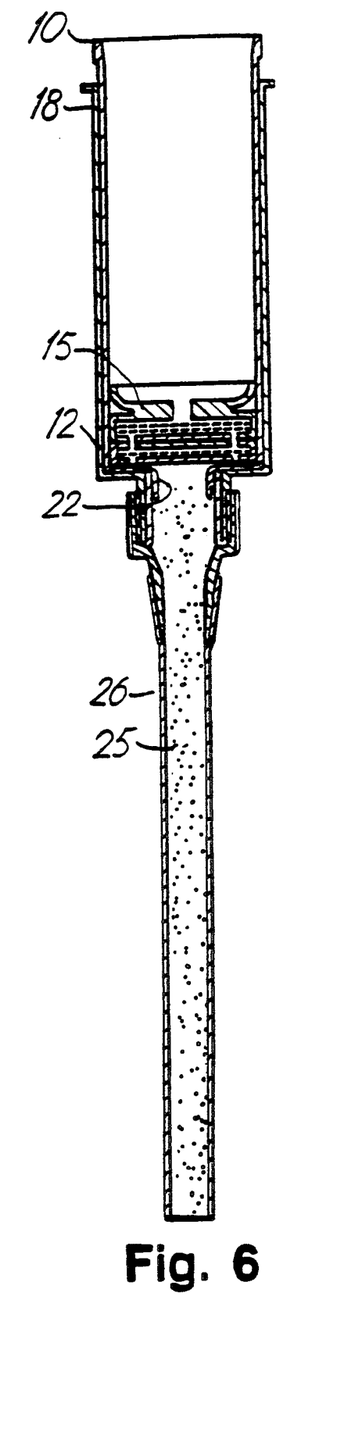

In FIG. 6 the piston formed by the pressure application disc 15 with the venting means 16 and by the filter assembly 12 has been moved to its fully extended position in which the filter assembly 12 is in abutting engagement with the inner surface of the inner end wall 13 of the inner cylinder 10. The membrane 22 has been broken, all of the mixture 25 has now been expelled from the inner cylinder 10 and the mixing device may be discarded.

Figures 7, 8, 9:
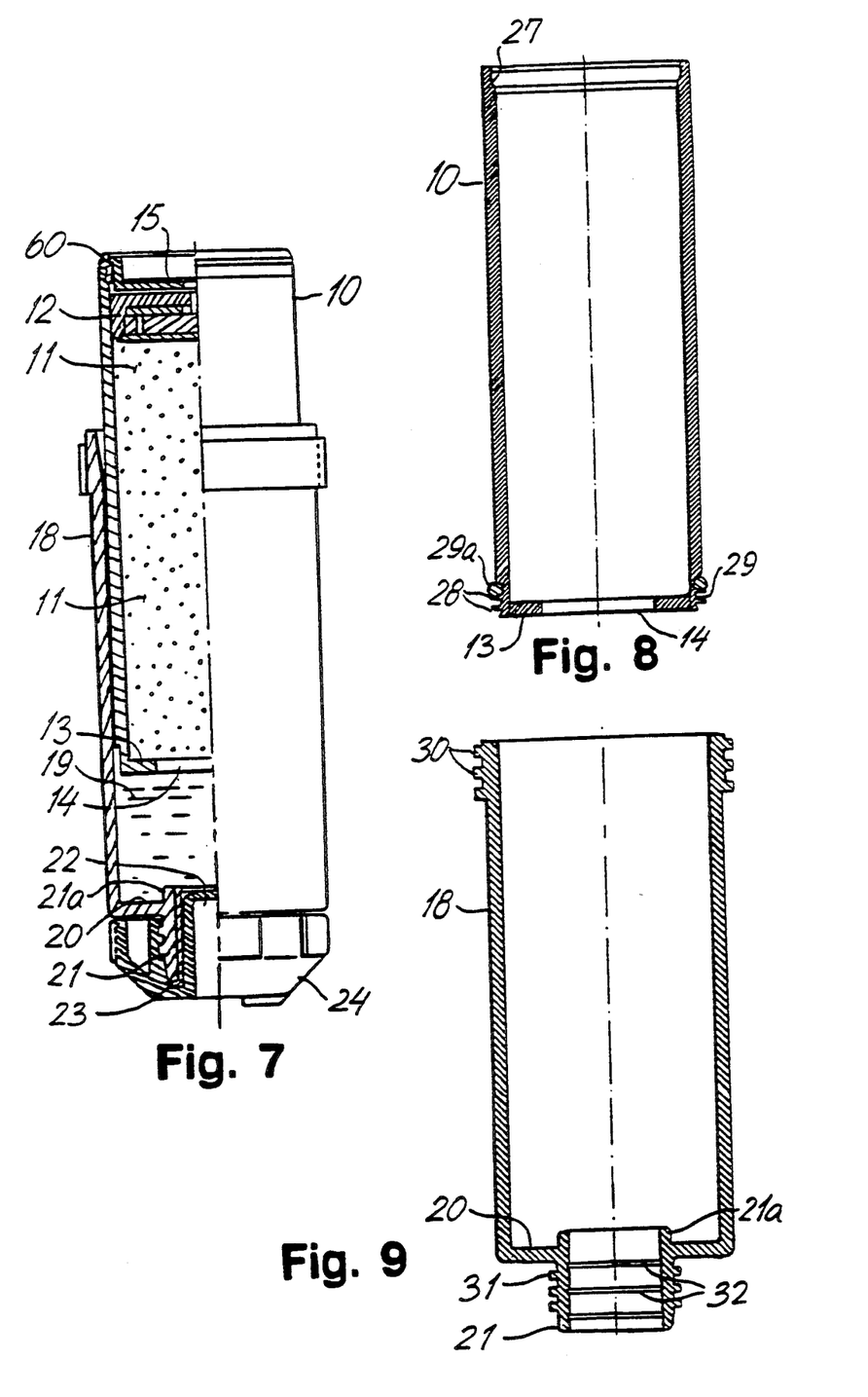
FIG. 7 is a side view and partially sectional view of a preferred embodiment of the mixing device according to the invention ready for use.
FIG. 8 is a sectional view of an inner cylinder of the device shown in FIG. 7.
FIG. 9 is a sectional view of an outer cylinder of the device shown in FIG. 7.

In FIGS. 7-22, parts corresponding to those shown in FIGS. 1-6 have been designated with similar reference numbers. In the embodiment shown in FIG. 7, the structure of the filter assembly 12 and of the pressure application disc 15 has been changed in relation to the embodiment shown in FIG. 1, and the assembly 12 and the disc 15 are arranged close together in the embodiment of FIG. 7. In other respects the structure as well as the function of the device shown in FIG. 7 are substantially the same as described above in relation to FIGS. 1-6. In the following, various parts of the mixing device will be described in more detail with reference to FIGS. 8-22.

FIG. 8 shows the inner cylinder 10 having its peripheral wall closed at one end by the end wall 13 and the breakable membrane 14. A locking groove 27 for locking the pressure application disc 15 in position as will be described in more detail below, is formed in the inner peripheral wall of the cylinder 10 at its open end. A pair of axially spaced annular sealing fins 28 for sealingly engaging with the inner peripheral wall of the outer cylinder 18 extend radially from an outer cylinder wall part 29 having a reduced outer diameter and defining the free end of the cylinder 10 adjacent to the end wall 13. The outer diameter of the annular, flexible sealing fins 28 slightly exceeds the maximum outer diameter of the peripheral wall of the cylinder 10. An O-ring 29a, which is arranged in a peripheral groove defined by the inner annular sealing fin 28 has a double purpose. Thus, the O-ring tends to maintain the adjacent fin 28 in a desired position in which the fin is in sealing engagement with the inner wall of the outer cylinder 18, when the inner cylinder is displaced in relation to the outer cylinder 18. Furthermore, the O-ring constitutes and additional seal between the inner and outer cylinder which is especially important during storage, when the fins 28 may tend to deform permanently.

FIG. 9 shows the outer cylinder 18 having external threads 30 for fixing the device into a discharge gun. The spout 21 extending axially from the end wall 20 has external threads 31 formed thereon, and a number of annular, axially spaced locking grooves 32 are formed in the inner peripheral wall of the spout 21. The spout 21 has an inward extension 21a projecting into the inner space of the outer cylinder 18, and the outer diameter of the extension 21a corresponds substantially to the inner cylinder of the central opening in the end wall 13 of the inner cylinder 10 so that all of the liquid component 19 is expelled from the outer cylinder 18, when the inner cylinder 10 is moved to its innermost position, vide FIG. 7.

Figure 12:
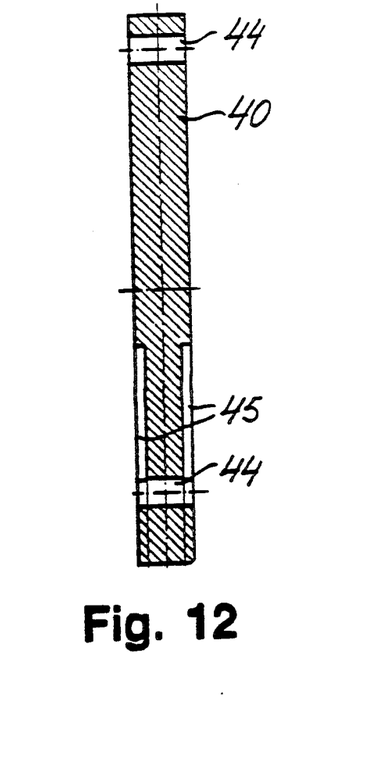
FIG. 12 is a sectional view of a filter backing or support plate of the filter assembly shown in FIG. 10.
Figure 13:
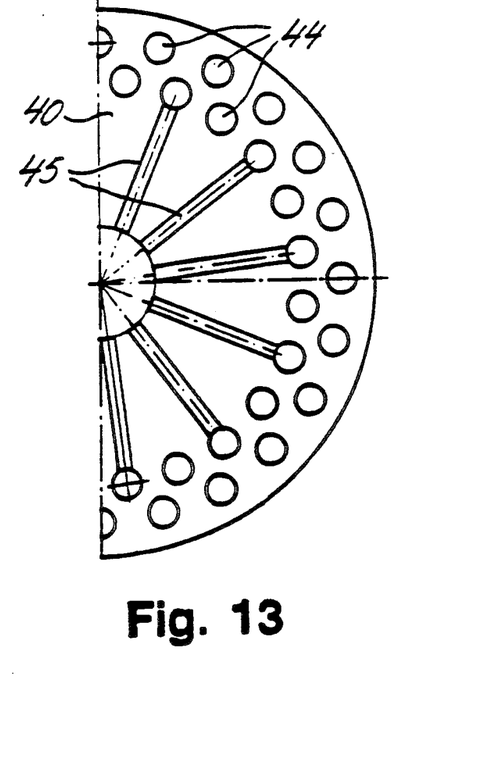
FIG. 13 is a plan view showing one half of the filter backing or support plate shown in FIG. 12.
Figure 14:
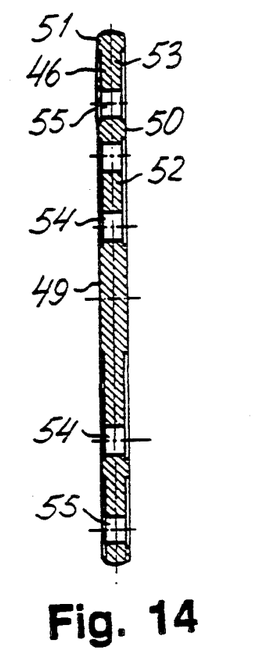
FIG. 14 is a sectional view of a filter retaining disc or lid plate of the filter assembly shown in FIG. 10.
Figure 15:
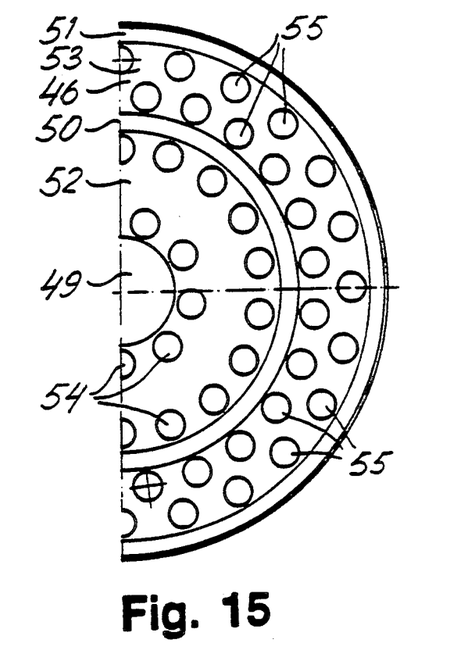
FIG. 15 is a plan view showing one half of a filter retaining disc or lid plate shown in FIG. 14, FIGS. 16 and 17 are a top plan view and a sectional view, respectively, of a pressure application disc for closing the outer end of the inner cylinder shown in FIG. 8.

As shown in FIGS. 10-15 the filter assembly 12 comprises a dish-shaped filter housing 33 including a disc member 34 and a skirt 35 extending axially therefrom. Axially spaced guide surface parts 36 are defined on the outer surface of the skirt and a pair of annular sealing fins or sealing lips 37 having a outer diameter exceeding the diameter of the guide surface parts 36 are positioned on either side of one of said guide surface parts 36. The filter assembly 12 is displaceably mounted in the inner cylinder 10 and the sealing fins 37 are then sealingly engaging with the inner peripheral surface part of the cylinder 10. Preferably, the sealing fins 37 are flexed towards the end wall 13 of the cylinder 10 when the assembly is mounted therein so as cause improved sealing efficiency when the inner pressure of the cylinder increases. The housing 33 shown in FIG. 11 further comprises an inner central boss 38 having a venting passage with radially directed inlet openings 39 formed therein. A filter backing plate 40 shown in FIGS. 12 and 13 is arranged within the housing 33 in abutting engagement with a narrow annular shoulder 41 and with the end surface of the boss 38 so as to define a filter chamber 42 which may be filled with a filtering medium 43, for example, a filter disc containing activated carbon. As best shown in FIG. 13 the backing plate 40 defines an annular arrangement of through-going openings or bores 44 adjacent to the rim portion of the backing plate 40. Grooves 45 extending radially inwardly from peripherally spaced bores 44 to the peripheral wall of the boss 38 are formed in opposite side surfaces of the backing plate 40. The open end of the dish-shaped filter housing 33 is closed by a perforated lid plate or closure plate 46 which is shown in FIGS. 14 and 15. The closure plate 46 may be pressed into the open end of the housing 33 and snapped behind an inner annular bead 47 formed on the skirt 35 of the housing 33 whereby the closure plate or lid plate 46 and also the backing plate 40 may be retained in their mounted position shown in FIG. 10. A filtering medium 48 may also be arranged in the space defined between the filter backing plate 40 and the closure plate 46. This filter medium may, for example, be a two-layer filter comprising an inner paper layer arranged adjacent to the backing plate 40 and an outer layer for example of cellulose nitrate, which is arranged adjacent to the closure plate or lid plate The closure plate or lid plate 46 has on its opposite side surfaces a central, raised abutment surface part 49, an annular abutment surface part 50 and an annular abutment surface part 51 positioned along the periphery of the lid plate 46. The raised surface parts 49, 50, and 51 are radially spaced and define annular wall parts 52 and 53 of reduced wall thickness therebetween. Patterns of through-going openings 54 and 55 are defined in the wall parts 52 and 53, respectively. Each of the plates 40 and 46 is symmetrical about its central plane and consequently, these plates cannot be incorrectly mounted.

Figure 10:
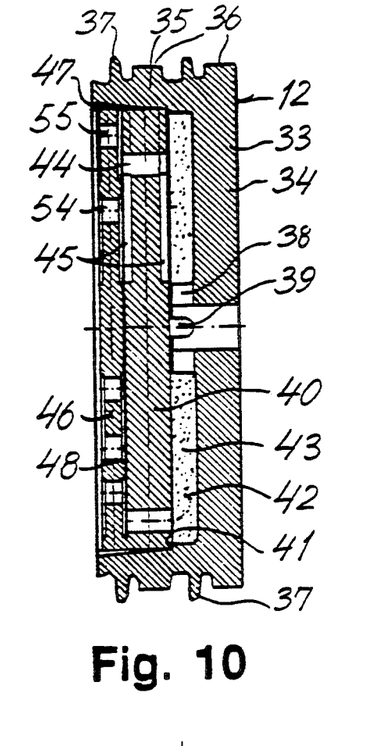
FIG. 10 is a sectional view of a piston-like filter assembly for cooperating with the inner cylinder of FIG. 8 and shown in an enlarged scale.
Figure 11:
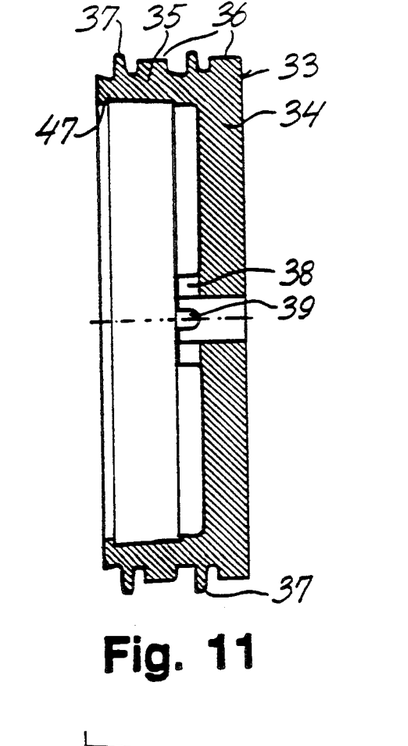
FIG. 11 is a sectional view of a piston-like filter housing of the assembly shown in FIG. 10.

When the filter assembly 12 and the pressure application disc 15 are pressed into the inner cylinder 10 to compact and expel the paste-like mixture 25 as described above with reference to FIGS. 4-6, gas and air may escape from the inner space of the cylinder 10 through the openings 54 and 55 in the closure plate or lid plate 46, the filtering medium 48, the openings or bores 44 in the backing plate 40, substantially radially through the filtering medium 43 in the filter chamber 42, and the filtered gas, which is now substantially free of dangerous substances, flows out into the ambient atmosphere through the venting passages formed in the boss 38. The radial grooves 45 in the backing plate 40 ensures a substantially uniform distribution of the air flow through the filtering medium 48. Because of the great number of bores or openings in the plates 40 and 46, the flow resistance in the filter assembly 12 shown in FIG. 10 is relatively low. This is important because a high air pressure within the cylinder 10 causes air to be dissolved in the paste-like mixture, whereby the quality of the mixture is adversely influenced. In case an excessive amount of the liquid component 19, which may, for example, be a liquid monomeric acrylate, tends to flow into the filter assembly 12 through the openings 54 and 55, it comes into contact with the cellulose nitrate filter causing the same to swell so as to prevent the liquid component from flowing through the filter assembly.

Figures 16, 17:
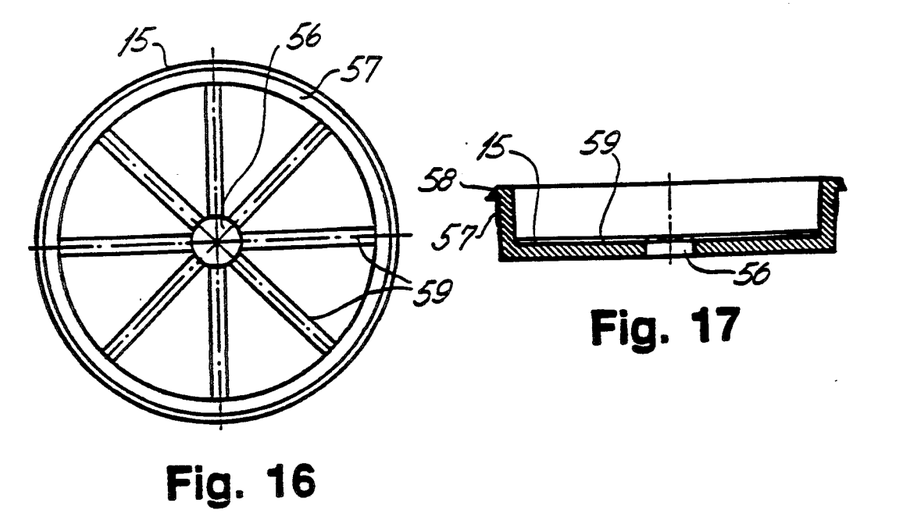

FIGS. 16 and 17 show the dish-shaped pressure application disc 15 defining a central venting opening 56 therein and having an axially extending skirt portion 57. A radially outwardly extending annular locking bean or flange 58 is formed at the free end of the skirt portion 57. A plurality of peripherally spaced grooves 59 defined in the outer side surface of the disc 15 extend from the venting opening 56 to the inner wall of the skirt portion 57. These grooves allow gas to escape from the venting opening 56 into the ambient atmosphere when the outer side surface of the disc 15 is engaged by a pressure plate or pressure head covering the venting opening 56.

Figure 18:
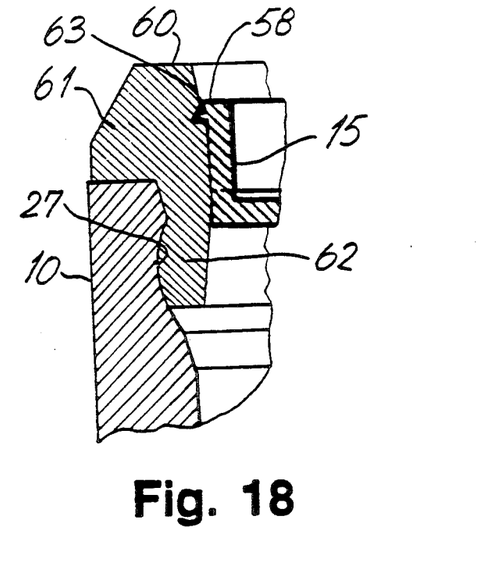
FIG. 18 is a partial sectional view shown how the pressure application disc is mounted in the outer end of the inner cylinder shown in FIG. 8, FIGS. 19 and 20 are a plan view and a longitudinal sectional view, respectively, of a tubular insert member with a breakable membrane for closing a spout opening of the outer cylinder shown in FIG. 9.
Figure 19:
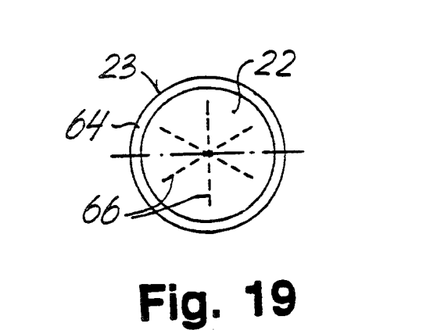

As shown in FIG. 18, the pressure application disc 15 is mounted at the open end of the inner cylinder 10 by means of an annular locking member 60 comprising a flange part 61 in abutting engagement with the end surface of the inner cylinder 10 and a stopper part 62 which is sealingly received in the open end of the cylinder 10. The outer peripheral surface of the stopper part 62 is shaped substantially complementary to the adjacent inner peripheral surface part of the inner cylinder 10 so that the stopper part 62 of the locking member 60 is in locking engagement with the inner annular locking groove 27 defined at the open end of the inner cylinder 10 as shown in FIG. 8 so as to retain the locking member 60 in position. The outer annular flange 58 of the pressure application disc 15 is in locking engagement with a complementary shaped inner annular locking groove 63 formed at the outer end of the annular locking member 60 as shown in FIG. 18. When an outer axial pressure is applied to the pressure application disc 15, the flange 58 is flexed upwardly and inwardly so that the disc 15 may be pushed into the cylinder together with the filter assembly 12 in a piston-like manner as described above with reference to FIGS. 4-6. The outer end of the inner wall of the cylinder 10 is conically widened so as to facilitate insertion of the locking member 60 and the filter assembly 12 into the cylinder.

Figure 20:
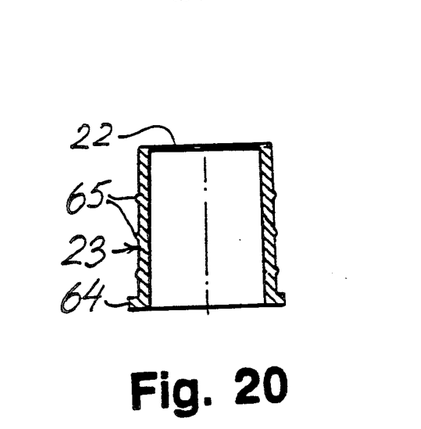

The tubular insert member 23 with the breakable membrane 22 is shown in more detail in FIGS. 10 and 20. The insert member 23 comprises a radially outwardly extending flange 64 positioned at the end of the insert member opposite the membrane 22 and a number of axially spaced, annular outer locking beads 65 fitting into the annular locking grooves 32 when the insert member 23 is pressed into the spout 21 of the outer cylinder 18. In the mounted position, the flange 64 engages with the outer end surface of the spout 21.

When the particulate material 11 has been filled into the inner cylinder 10, the inner cylinder is closed by means of the filter assembly 12 and the pressure plate 15. Thereafter, the inner cylinder is inserted into the outer cylinder 18 while the bore of the spout 21 is still open. In this condition the mixing device may be sterilized, for example, by gamma radiation. After sterilization, the liquid component or monomer 19 is filled into the outer cylinder through the open spout 21 which is thereafter closed by means of the insert member 23. The inner wall of the spout 21 preferably has a conical shape so that a tight fit is not obtained between the outer peripheral surface of the insert member and the inner surface of the spout 21 until the insert member has been almost fully inserted. Thereby inclusion of a bubble of compressed air in the outer cylinder may be avoided. Such air bubble could adversely influence the quality of the final mixture as previously described.

The membrane 22 may be of any suitable material, such as a plastic film or metal foil or a laminate of such materials fastened to the end surface of the annular insert member 23. Alternatively, the membrane 22 may be a thin wall part moulded integrally with the cylindrical wall of the insert member. In order to reduce the pressure necessary to break the membrane 22, such membrane may be provided with a pattern of weakening lines or predetermined breaking lines 66 indicated by dotted lines in FIG. 19. Such weakening lines may be linear or curved depressions or grooves defined in a side surface of the membrane. As an example, the membrane 22 may be of a plastic material and have a thickness of about 0.25 mm and the predetermined breaking lines may be grooves having a depth of about 0.1 mm.

Figure 21:
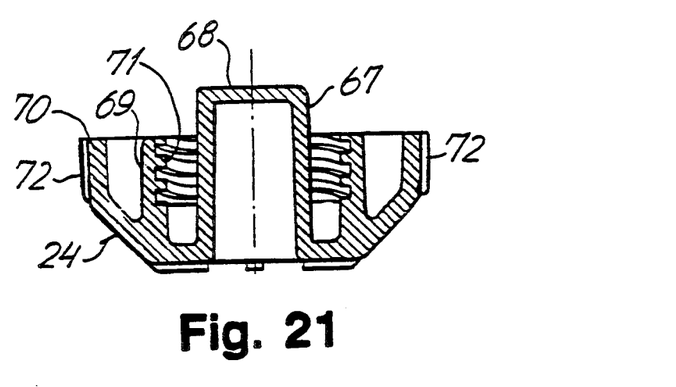
FIG. 21 is a sectional view of a membrane supporting member to be mounted on the spout of the outer cylinder during storage and use of the mixing device prior to expelling the contents of the device.

The cap-like membrane supporting member 24 which is shown in FIG. 21 comprises a central cylinder part 67 having a membrane supporting end wall 68. Radially spaced inner and outer skirt parts 69 and 70 surround the central cylinder part and are radially spaced therefrom. The inner skirt part 69 is provided with internal threads 71 for engaging with the external threads 31 of the spout 21 of the outer cylinder 18. The outer skirt part 70 of the membrane supporting member 24 is provided with outer projections 72 facilitating screwing and unscrewing of the cap-like member.

Figure 22:
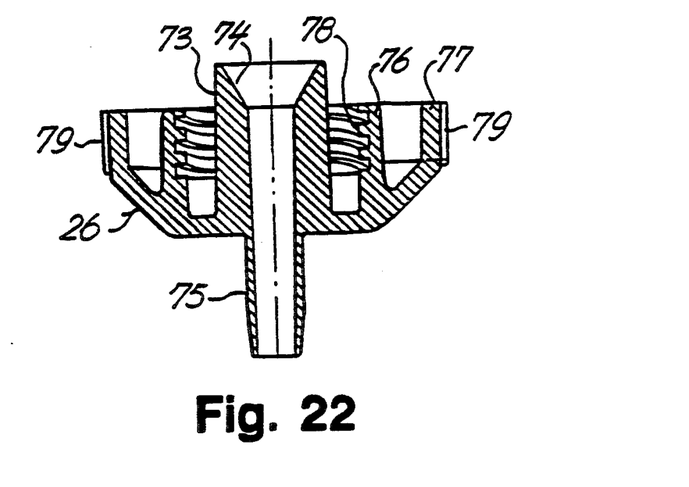
FIG. 22 is a longitudinal sectional view of a nozzle member to be screwed on the spout of the outer cylinder during use of the mixing device.

FIG. 22 illustrates a modified embodiment of the discharge nozzle 26 shown in FIG. 5 and 6. The discharge nozzle comprises a central cylinder part 73 defining a central bore with a funnel-like opening 74 at its free end. The inner bore of an oppositely extending nozzle tube 75 forms a continuation of the inner bore of the central cylinder part 73. The central cylinder part 73 is surrounded by mutually spaced inner and outer skirt parts 76 and 77. The inner skirt part 76 is provided with internal threads 78 which may engage with the outer threads 31 of the spout 21 formed on the outer cylinder 18. The outer skirt part 77 comprises outer projections 79 facilitating screwing and unscrewing of the discharge nozzle 24. Thus, the inner and outer skirt parts 76 and 77 correspond to the inner and outer skirt parts 69 and 70 of the membrane supporting member 24. The axial length of the central cylinder part 73 is somewhat smaller than the length of the central cylinder part 67 of the supporting member 24, so that the membrane 22 is not supported or ruptured by the cylinder part 73.

When the mixture 25 has made and compacted as described above the supporting member 24 is replaced by the discharge nozzle 26 as previously explained. When the nozzle 26 is screwed on the spout 21 the central cylinder part 73 is inserted into the inner bore of the spout without contacting the membrane 22. When a sufficiently high expelling force is applied to the mixture 25 by means of the piston-like assembly 12, 15 as previously described the membrane 22 breaks so that the mixture may be expelled through the nozzle tube 75 which may have any desired length. If desired, and additional tube length may be mounted on the nozzle tube 75.

It should be understood that when the mixing device is used for mixing types of mixtures other than bone cement, the central cylinder part 73 could have a cutting free edge and such an axial length that it would automatically cut the membrane 22 when the discharge nozzle 26 is mounted on the spout 21.

The parts of the mixing device described above may be made from any suitable material, such as metal. However, the various parts of the mixing device apart from the various filters are preferably made from plastic.

EXAMPLE

The mixing device shown in FIG. 7 may be used for mixing the components of bone cement. The outer cylinder 18 may have an inner diameter of about 40 mm and a wall thickness exceeding 1.5 mm and preferably exceeding 2.5 mm. The wall thickness of the end wall 20 of the outer cylinder is preferably about 10 percent thicker and may be, for example, 2–3.5, preferably 2.5–3.2 mm. The non-supported area of the breakable membrane 14 comprised by the inner cylinder 10 should be sufficiently large to ensure that the membrane breaks when exposed to a desired relatively low pressure. When the membrane 14 is made from aluminum foil having a thickness of $50\mu$, the circular opening defined by the inner end wall 13 of the inner cylinder 10 and being closed by the membrane 14 should have a diameter of about 20–25 mm, preferably about 22–23 mm. A substantially smaller diameter partly causes the liquid component of the mixture not to distribute uniformly over the cross sectional area of the inner cylinder 10, and partly an undesirable increase of the pressure necessary to break the membrane, and a substantially larger diameter causes the annular end wall 13 to be rather narrow so that it will be difficult to obtain a sufficiently reliable seal between the rim portion of the membrane and the annular end wall 12 of the inner cylinder 10.

The membrane 14 has a strength so that it breaks when an axially inwardly directed pressure ob 0.8–1.0 kN is applied to the inner cylinder. Since that pressure is applied to the pressure plate 15, the releasable interlocking of the bean or flange 58 of the pressure plate and the locking groove 63 should be sufficiently strong so that the locking is not released until a substantially higher pressure, for example, 1.5 kN, is applied to the pressure plate 15.

The filtering medium 43 as well as the filtering medium 48 should be sufficiently gas-penetrable to avoid creation of a high gas pressure within the inner cylinder 10. The filtering medium may be a two-layer filter comprising an inner paper layer such arranged adjacent to the backing plate 40 and an outer layer as cellulose nitrate arranged adjacent to the closure plate. The pore size of the paper layer is $0.2-5\mu$, preferably $0.4-1\mu$ for example $0.65\mu$. The pore size of cellulose nitrate is within the same ranges or is even greater.

It should be understood that various amendments and modifications of the embodiments described above and shown in the drawings could be made without departing from the scope of the present invention. As an example, the membrane 22 could be replaced by a manually operatable valve or the central cylinder part 73 could be adapted to puncture of cut the membrane 22 when the discharge nozzle 26 is mounted on the spout 21. Similarly, the breakable membrane 14 could be dispensed with and replaced by other means for communicating between the inner spaces of the cylinders 10 and 18 when the particulate and liquid components are to be mixed. Such communications means could, for example, be a valve or stopper which could be opened by pulling a string extending through the filter assembly 12 and the venting opening of the disc 15. While the mixing device according to the invention has been particularly described with reference to mixing of components of bone cement, it should be understood that the mixing device according to the invention could also be used for mixing other kinds of components for forming a mixture thereof, which mixture could, for example, be packing, jointing, sealing, caulking, or filler compounds. Furthermore, parts of the embodiments described may be changed or modified and dimensions may be chosen dependent on the field of application.

We claim:

1. A method of preparing a mixture of a solid, particulate or powdered first component and a liquid second component so as to provide a paste-like material, said method comprising:
arranging the first component in a first cylinder, the size of particles of said first component being such that coherent liquid-receiving interstices are defined therebetween;
arranging the liquid second component in a second cylinder having a closed first end and an opposite second end, a first end of the first cylinder being arranged in the second end of the second cylinder in a piston-like manner and in sealing relation thereto;
forcing said liquid second component into the first cylinder by relatively moving the first cylinder towards the closed end of the second cylinder while venting the first cylinder at a second end of the first cylinder opposite to said first end thereof, whereby the liquid second component is received in said interstices in said first component thereby mixing said first and second components together, said step of mixing including venting any gaseous material in said first cylinder to the atmosphere during said relative movement thereby to achieve a substantially homogeneous mixture comprising said paste-like material; and
subsequently expelling said mixture of said first component and said liquid second component mixed to form said paste-like material from the first cylinder, said step of expelling comprising forcing said paste-like material toward said closed end of said second cylinder, said closed end of said second cylinder having a discharge orifice disposed therein, through which said paste-like material is discharged.

2. A method according to claim 1, wherein the mixture is compacted prior to expelling.

3. A method according to claim 1, wherein the mixture is allowed to mature for a predetermined period of time prior to expelling.

4. A method according to claim 1, wherein the step of venting the first cylinder comprises venting through a gas-permeable wall part or filter impermeable to the particles of the first component.

5. A method according to claim 1, wherein the size of the main part of the particles of the first component arranged in the first cylinder is between 15 and 300$\mu$.

6. A method according to claim 1, wherein the size of the particles of the first component arranged in the first cylinder is between 25 and 250$\mu$.

7. A method according to claim 1, wherein the size of the particles of the first component arranged in the first cylinder is between 50 and 200$\mu$.

8. A method according to claim 1, wherein a rupturable wall is disposed in the first end of the first cylinder, and said step of forcing the liquid second component into the first cylinder comprises rupturing said wall by the step of relatively moving said first cylinder towards the closed end of the second cylinder and further wherein said step of expelling comprises moving a piston member disposed in the first cylinder toward the closed end of the second cylinder.

9. A method according to claim 1, wherein the paste-like material is an acrylate bone cement composition.

10. A method according to claim 1, wherein the step of expelling further comprises breaking a rupturable seal disposed at said discharge orifice thereby allowing the discharge of said paste-like material through said discharge orifice.

11. A method according to claim 10, wherein the step of breaking the rupturable seal comprises moving said piston member in said first cylinder, thereby rupturing said rupturable seal.

12. A mixing device for mixing a solid, particulate or powdered first component and a liquid second component so as to provide a paste-like material therefrom, said device comprising:
a first cylinder for containing said first component and having a first end and an opposite second end provided with venting means;
a second cylinder for containing said liquid second component and having a first end and an opposite second end sealingly receiving the first end of the first cylinder in a piston-like manner;
means for providing communication between inner spaces of the first and second cylinders through at least one of said first end of the first cylinder and said second end of said second cylinder, thereby allowing the liquid second component from the second cylinder to be injected into interstices defined between particles of the first component contained in the first cylinder for providing said paste-like material, when said first cylinder is relatively moved into the second cylinder;
said venting means comprising means for allowing gaseous matter to be removed to the atmosphere from said first cylinder during relative movement of said first and second cylinders thereby allowing said first and second components to mix to form a substantially homogeneous mixture comprising said paste-like material in said first cylinder; and further comprising:
a discharge orifice at the closed first end of the second cylinder for providing said paste-like material from said first cylinder; and
means for expelling said mixed paste-like material out of the first cylinder through the orifice.

13. A device according to claim 12, wherein the expelling means comprises a piston member displaceably arranged in said second end of the first cylinder.

14. A device according to claim 13, wherein said piston member comprises releasable locking means for retaining the piston member immobile in relation to the first cylinder, the locking means being released when the piston member is exposed to a second inwardly directed axial pressure substantially exceeding said predetermined first differential pressure.

15. A device according to claim 14, wherein said locking means comprise one or more projections extending radially from the piston member and engaging with the first cylinder or a member connected thereto.

16. A device according to claim 15, wherein said radial projections comprise a flexible annular collar member or bead.

17. A device according to claim 14, wherein a wall part of the closed first end of the second cylinder comprises rupturable means which is breakable when exposed to a predetermined third differential pressure.

18. A device according to claim 17, further comprising a removable back-up member arranged in supporting engagement with the outer surface of said breakable wall part of the closed first end of the second cylinder for preventing premature rupturing of said breakable wall part.

19. A device according to claim 12, wherein the means for providing communication comprises a wall part of the first end of the first cylinder which is breakable when exposed to a predetermined first differential pressure.

20. A device according to claim 19, wherein said breakable wall part is a breakable membrane.

21. A device according to claim 19, wherein a wall part of the closed first end of the second cylinder comprises rupturable means which is breakable when said means for expelling forces said paste-like material against said rupturable means.

22. A device according to claim 13, wherein the venting means is arranged in said piston member.

23. A device according to claim 22, wherein said venting means comprises vapor-absorbing filtering means.

24. A device according to claim 23, wherein said filtering means comprises activated carbon.

25. A device according to claim 12, wherein said expelling means comprises a piston-like filter device which is displaceably arranged within the first cylinder for defining a first component material-receiving space between the filter device and said closed first end of the first cylinder.

26. A device according to claim 25, wherein the filter device comprises filtering means which is penetrable to gas, but impervious to liquid.

27. A device according to claim 26, wherein the filtering means comprises a filtering medium which swells when contacted by the liquid component.

28. A device according to claim 12, wherein the first component and the liquid second component are components forming bone cement when mixed.

29. A device according to claim 28, wherein the first component contained in the first cylinder comprises a polymer component having particles of a size between 15 and 300µ.

30. A device according to claim 29, wherein the size of the particles of the polymer component contained in the first cylinder is between 25 and 250µ.

31. A device according to claim 30, wherein the size of the particles of the polymer component contained in the first cylinder is between 50 and 200µ.

32. A device according to claim 12, wherein the first cylinder contains a polymer component comprising (meth)acrylate polymers or copolymers or a mixture thereof and wherein the second cylinder contains a liquid monomeric (meth)acrylate.

33. A device according to claim 32, wherein the polymer component further comprises X-ray contrast particles.

34. A device according to claim 12, wherein the means for providing communication comprises a wall part of the first end of the first cylinder which is breakable during relative movement of the first and second cylinders.

35. A device according to claim 12, wherein a wall part of the closed first end of the second cylinder comprises rupturable means which is breakable when said means for expelling forces said paste-like material against said rupturable means.

36. A device according to claim 35, further comprising a removable back-up member arranged in supporting engagement with the outer surface of said breakable wall part of the closed first end of the second cylinder for preventing premature rupturing of said breakable wall part.

* * * * *